United States Patent [19]

Sharp

[11] 4,028,728
[45] June 7, 1977

[54] METHOD OF AND VIDEO SYSTEM FOR IDENTIFYING DIFFERENT LIGHT-REFLECTIVE SURFACE AREAS ON ARTICLES

[75] Inventor: Benny H. Sharp, Yukon, Okla.

[73] Assignee: Western Electric Company, Inc., New York, N.Y.

[22] Filed: Apr. 2, 1976

[21] Appl. No.: 672,914

[52] U.S. Cl. .............................. 358/106; 358/107; 356/237; 250/225; 250/562
[51] Int. Cl.[2] ......................................... H04N 7/18
[58] Field of Search ............ 358/100, 88, 101, 106, 358/107; 178/DIG. 36, DIG. 1, DIG. 37, DIG. 38; 235/111.3; 250/560, 562, 565, 225; 350/153; 356/237

[56] References Cited
UNITED STATES PATENTS 3,713,741  1/1973  Sheehan ............................ 356/237

OTHER PUBLICATIONS

W. P. Shaw, *High–Speed Automatic Particle Counter*, 2–75, p. 2588, I.B.M. Technical Disclosure Bulletin.

E. E. Haas, *Surface Defect Detector*, 1–72, p. 37, Western Electric Tech. Dig. No. 25.

*Primary Examiner*—Robert L. Griffin
*Assistant Examiner*—Edward L. Coles
*Attorney, Agent, or Firm*—K. R. Bergum; R. P. Miller

[57] ABSTRACT

Article surface defect detection methods and closed-circuit video systems for use therewith are disclosed for discriminating between different types of light-reflective surface areas on articles. Such methods and systems are particularly adapted to ascertain the presence and absence of, as well as condition of, circuit paths and satisfactory versus unsatisfactory soldered connections on printed circuit boards. In order to optimize the contrast between such two-dimensional and three-dimensional light-reflective surface areas, a specially oriented and polarized screen is interposed between the light source and article surface to be examined, and a rotatably adjustable polarized filter is preferably mounted on the camera, with the axis of the lens system thereof being oriented substantially perpendicularly to both the polarized light rays and the exposed article surface to be examined.

29 Claims, 14 Drawing Figures

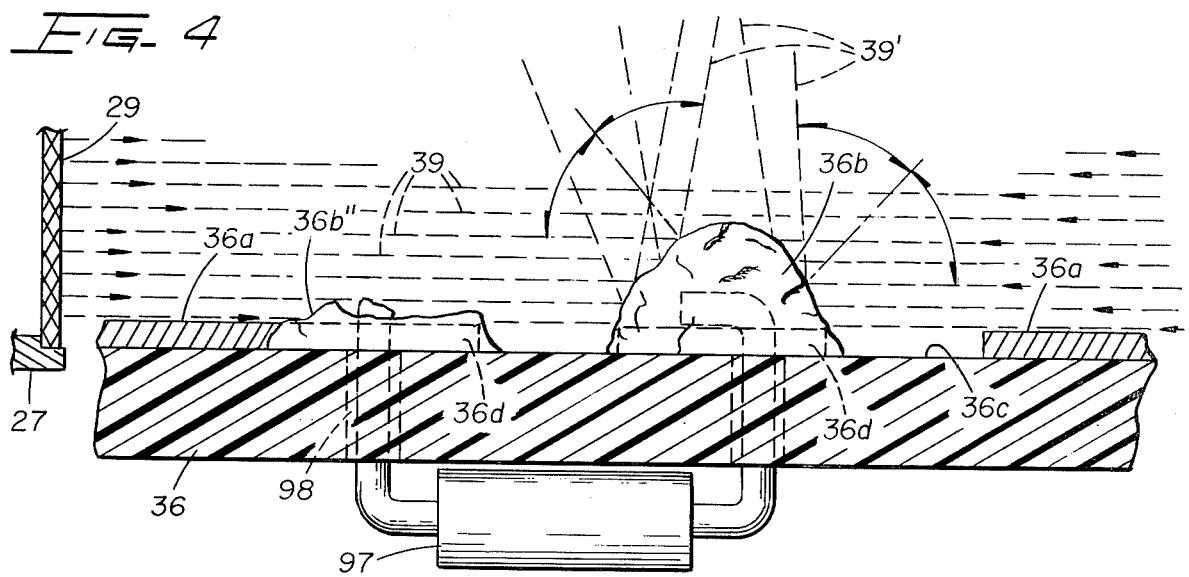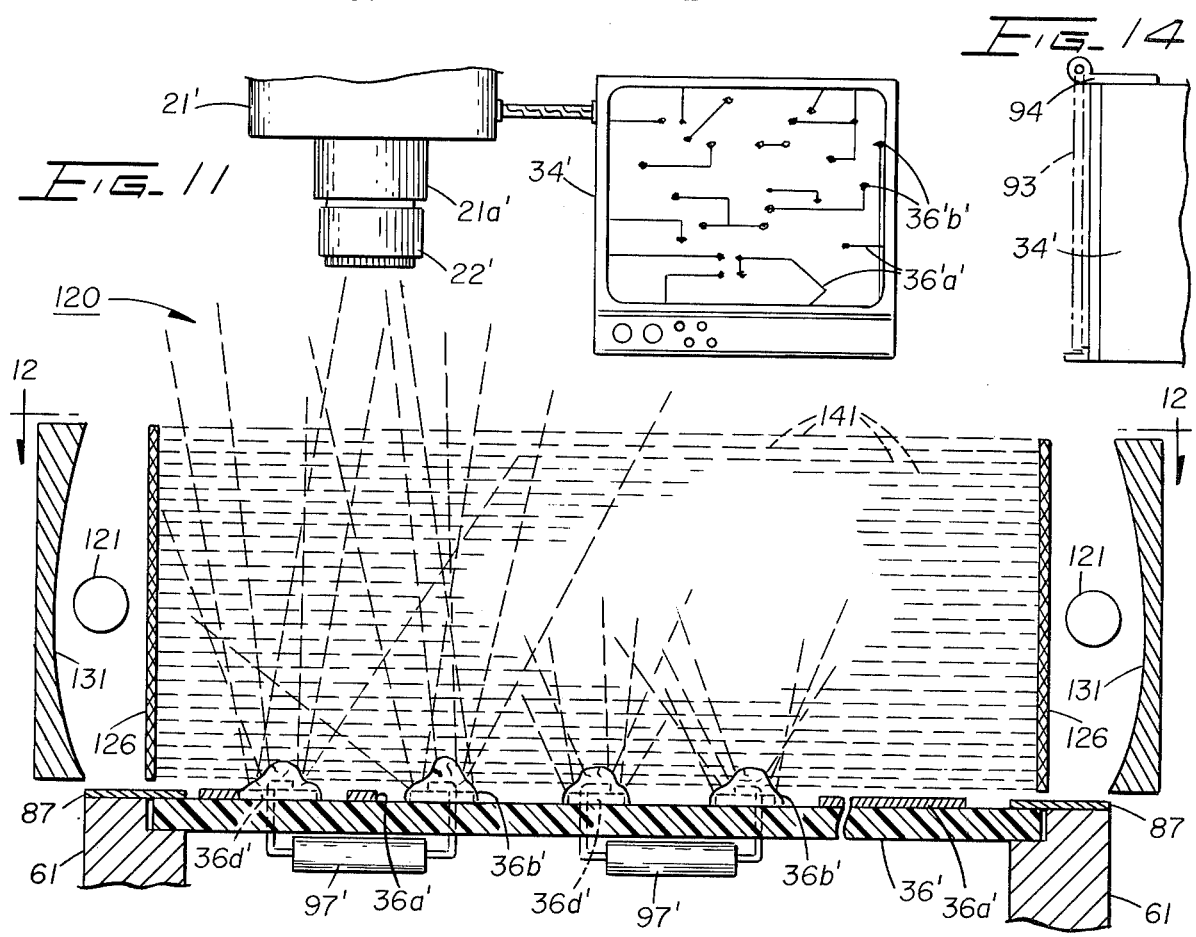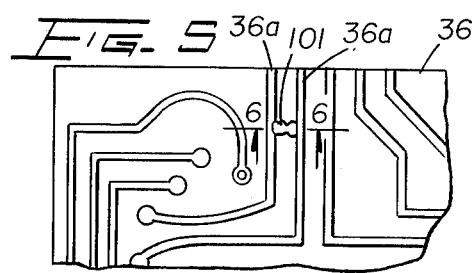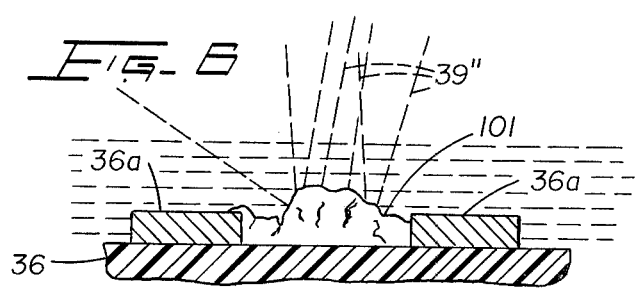

METHOD OF AND VIDEO SYSTEM FOR IDENTIFYING DIFFERENT LIGHT-REFLECTIVE SURFACE AREAS ON ARTICLES

BACKGROUND OF THE INVENTION

1. Field of the Invention

This invention relates to an article surface defect detection system and, more particularly, to a method of and video system for discriminating between different types of light-reflective surface areas on articles, such as involved in ascertaining the presence and absence of, as well as condition of, circuit paths and satisfactory versus unsatisfactory soldered connections on printed circuit boards.

2. Description of the Prior Art

The simplest way to ascertain whether all of the areas that should be soldered have been on a printed wiring board and, if soldered, whether the soldered connections are satisfactory or not, is to visually examine each connection, preferably through a magnifying lens, with special attention being given to the surface area profile of each connection. More specifically, the profile of a typical satisfactory soldered connection should appear as a relatively smooth and uniformly contoured solder fillet. An examination of the profile of each soldered connection (fillet) can also provide quite accurate information as to whether or not any clinched lead end of a solder-connected component is present and, if so, whether it is properly oriented, cut to the desired length, and is of the clinched type, biased firmly against the wiring board.

In addition to examining a printed wiring board for any possible solder defects, it is also normally important that the printed circuitry per se be examined (at least visually scanned) for any possible defects therein, such as open circuits, or solder bridges, or icicles, that can produce short circuits between adjacent circuit paths.

It becomes readily apparent that when a direct visual examination procedure is employed, it is not only very time consuming and tedious, but involves considerable eye strain, notwithstanding the use of any magnifying lens. Compounding the problem of eye strain is the fact that with respect to circuit boards having very high density circuitry fabricated thereon, the spacing between adjacent soldered connections and circuit paths is extremely close, often being less than several mils. This is particularly true in many microminiaturized electronic circuit packs employed in diverse types of electronic equipment and systems. High density printed circuitry, of course, also has a tendency to produce substantial light-reflected glare off of the relatively smooth surfaces thereof. Such glare can very readily establish blind spots that can significantly contribute to the defect-identification error rate, as well as contribute to operator fatigue.

Such problems, at least with respect to the examining of printed circuit boards, has been obviated to a great extent heretofore through the utilization of commercially available electronic scanners that employ either an incandescent light source, or a laser beam, in conjunction with a reflected light-receiving photodiode matrix, for example, to differentiate between different light-reflective surface characteristics on the board. In such scanner systems, the reflected light pattern read out of the photodiode matrix, representative of the scanned surface of the test specimen, is normally compared against a standard reference pattern previously read out of the matrix. Such a system is quite effective in descriminatng between flat, conductive printed circuit paths and the non-conductive surfaces of a circuit board. Systems of the described type, however, are not particularly useful after component assembly and soldering, as the resulting solder fillets, in terms of size and profile, present an infinite number of light-reflective variables and, hence, an infinite number of required matrix patterns, in order to reliably examine an entire circuit board, not to mention making a determination of even one satisfactory versus unsatisfactory soldered connection. The particular orientation of clinched lead ends also presents an infinite number of variables to any reflected light-responsive scanning system.

British Pat. No. 727,480 discloses a TV or video system for viewing an entire object, as distinguished from a selected surface thereof, in the presence of scattered light caused, for example, by minute creatures or particles under water, or smoke particles in the atmosphere. The apparatus includes a light source for illuminating the object with a beam or beams of substantially parallel light projected downwardly onto the object (as distinguished from across a given surface to be viewed) in a direction substantially perpendicular to the axis of a TV camera. A light polarizing filter is suitably oriented in the path of the light (either between the light source and object or between the latter and the camera) to reduce the effect of scattered light on the camera. As arranged and operated, this prior video system can only discriminate between the environment (with the minute particles, for example, causing the scattered light) and the entire object which is intended to be seen as clearly as possible.

SUMMARY OF THE INVENTION

It, therefore, is an object of the present invention to provide a method of and video system for discriminating between light-reflective planar and profiled conductive surface areas normally formed on a common, substantially planar surface of an object in accordance with a predetermined pattern, as well as to provide a reliable visual indication of the presence or absence of either type of surface area thereon, and in a manner that minimizes eye strain and operator fatigue, even in high volume inspection applications.

It is a more specific object of the present invention to provide a method of and apparatus for rapidly and reliably ascertaining the presence and absence of, as well as condition of, conductive circuit paths and soldered connections on printed circuit boards.

In accordance with the principles of the present invention, the above and other objects are realized with a closed circuit video system which includes a video camera, a video monitor coupled thereto, a light source, a polarized screen and an indexable table on which articles, such as printed circuit boards, are successively mounted for examination.

Considered more specifically with reference to a printed circuit (or wiring) board inspection application, the polarized screen is interposed between the light source and the circuit board, and oriented substantially normal to the exposed surface of the latter so as to effect the vertical polarization of the light passed therethrough. Such light is thus projected as parallel light rays formed in discrete, vertically oriented planes across the exposed surface of the circuit board. The video camera, preferably employed with a polarized lens (or filter) attached thereto, is mounted in a spaced, overlying position relative to the circuit board, with the optical axis of the camera oriented perpendicularly relative to the exposed, patterned surface of the circuit board.

Such a system significantly results in all substantially planar conductive circuit path areas on the board, as well as missing solder connections, being substantially nonreflective in the direction of the camera and, thus, appearing as dark gray or black areas on the screen of the TV monitor, when operating in a black and white mode, against the contrasting lighter (but not bright) background representative of the exposed non-conductive circuit board surface areas. Conversely, all sufficiently raised surfaces, such as satisfactory soldered connections having a profile in the form of fillets around properly clinched component lead ends, as well as circuit-shorting bridges or icicles, appear as very bright, sharply defined white areas on the monitor. Either improperly oriented and/or clinched component lead ends whether soldered or not, or improperly oriented, but normally upstanding lead ends without solder, will also appear as bright areas on the monitor.

The desired presence of the readily seen bright areas on the monitor, or their absence, are normally immediately recognized as being in the proper or improper locations, and indicative of satisfactory or unsatisfactory surface conditions, by an operator with very little training, particularly when the circuitry is of a simplified nature. If desired or necessary, of course, the desired locations of not only the viewed bright areas, but of all conductive circuit path areas, may be directly compared against a composite reference pattern.

Advantageously, the subject system is relatively inexpensive and simple to operate, and has the advantage over the aforementioned known types of commercially available electronic scanning systems in being able to distinguish between substantially planar (two-dimensional) and profiled (three-dimensional) surface areas, rather than simply sensing for the presence, or absence, of planar, light-reflective patterned areas per se.

In addition, because of the present system's high resolution and light-reflective surface profile discrimination characteristics, it has also been found to be capable of locating deleterious scratches, pin holes or pits in otherwise smooth, and even highly polished, conductive surfaces, such as gold contact fingers or tabs formed along one or more edges of printed circuit boards. With such a high degree of sensitivity to reflected light, the subject system is seen to have utility in making very accurate and demanding quality examinations of various types of light-reflective surfaces on diverse articles.

BRIEF DESCRIPTION OF THE DRAWINGS

FIG. 4 is an enlarged, fragmentary detail view, partially in section, showing typical satisfactory and unsatisfactory soldered connections associated with a given component mounted on a circuit board being examined, with representative incident and reflected light rays being selectively associated with the distinctively different soldered connections in accordance with the principles of the present invention;

FIG. 5 is a fragmentary plan view of a representative printed circuit board, and illustrates a typical solder bridge that can cause a short circuit between two adjacent circuit paths as formed on the circuit board;

FIG. 6 is an enlarged, fragmentary detail sectional view, taken along the line 6—6 of FIG. 5, illustrating in greater detail the profile of the solder bridge of FIG. 5, with several representative incident and reflected light rays associated therewith, some of which reflected rays are directed toward the video camera in accordance with the principles of the present invention;

FIG. 8 is a pictorial view of a vacuum-operated dot marking mechanism applicable for use with the video identification systems embodied in FIGS. 1 and 11;

FIG. 9 is an enlarged, detail fragmentary view of the dot-carrying tape transport of FIG. 8;

FIGS. 11 and 12 are enlarged, front and plan views, respectively, both partially in section, of an alternative video system incorporating the same basic system elements depicted in FIGS. 1–3, but distinguishing therefrom by incorporating two pairs of mutually disposed light sources of the elongated, tubular bulb type, and a pair of flat, rectangularly shaped polarized screens respectively interposed between the light sources and the illustrative circuit board under examination in accordance with the principles of the present invention;

FIG. 14 is a fragmentary, side elevational view of a TV monitor similar to the ones depicted in FIGS. 2 and 11, but further including a pivotal holder secured thereto for supporting a patterned reference mask or transparency thereon that allows close proximity comparisons to be made between the reference pattern and the light reflected pattern representative of the actual printed circuit on the board under examination.

DETAILED DESCRIPTION OF THE INVENTION

It should be appreciated that the methods and video inspection systems as embodied herein, and described in greater detail hereinbelow, have universal application in examining and discriminating between different light-reflective profiled surface areas on diverse types of articles. However, for purposes of illustration, the subject invention is disclosed herein in connection with one preferred application, namely, in examining fabricated printed circuit boards for defects, such as unsatisfactory soldered connections, circuit path discontinuities, short circuiting bridges, and deleterious conductive surface scratches or pits.

Figure 1:
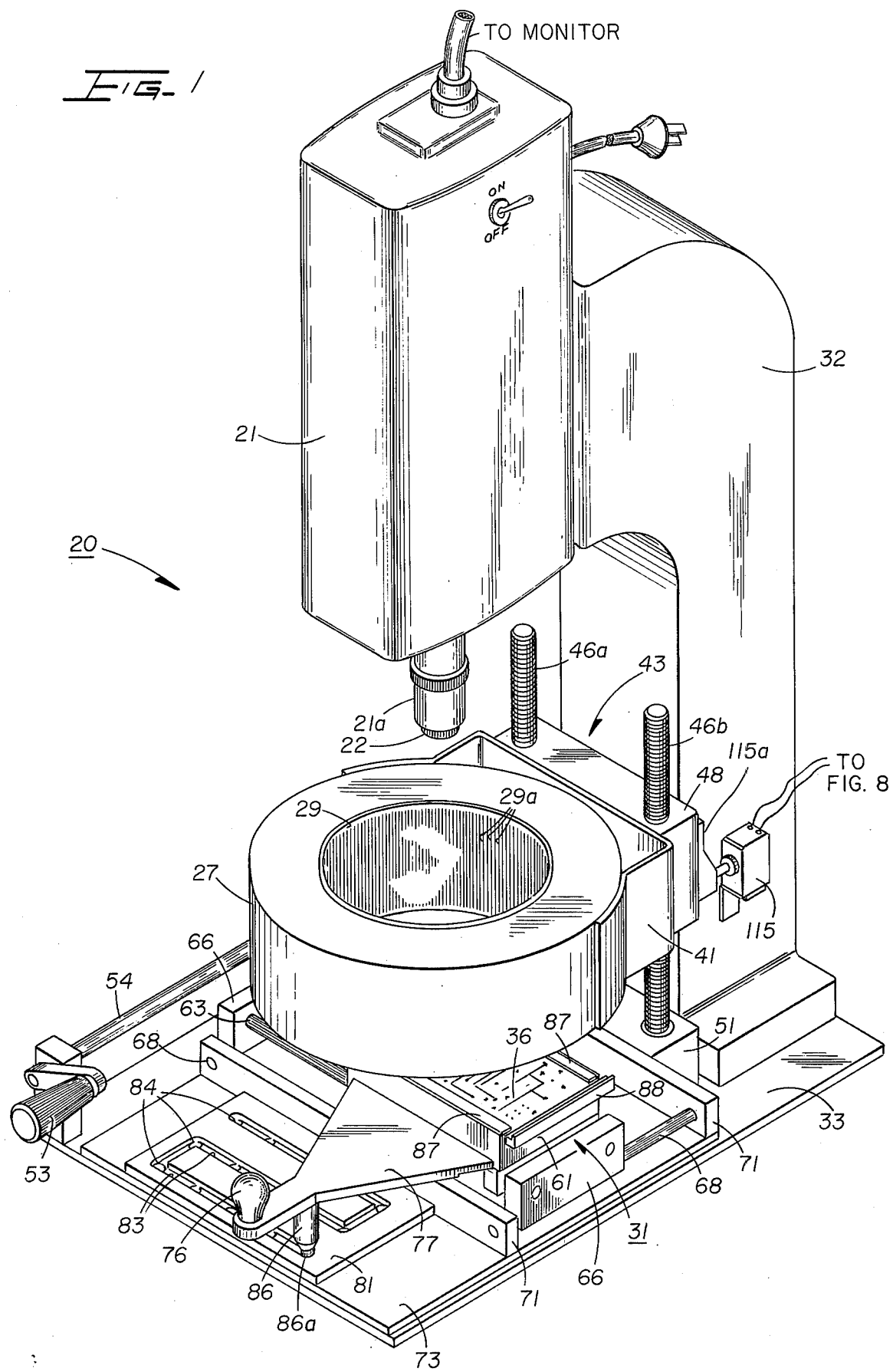
FIG. 1 is a perspective view of the main portion of a video system for examining circuit boards for solder defects, as well as other differentiating light-reflective defects, in accordance with the principles of and one preferred embodiment of the invention.
Figure 2:
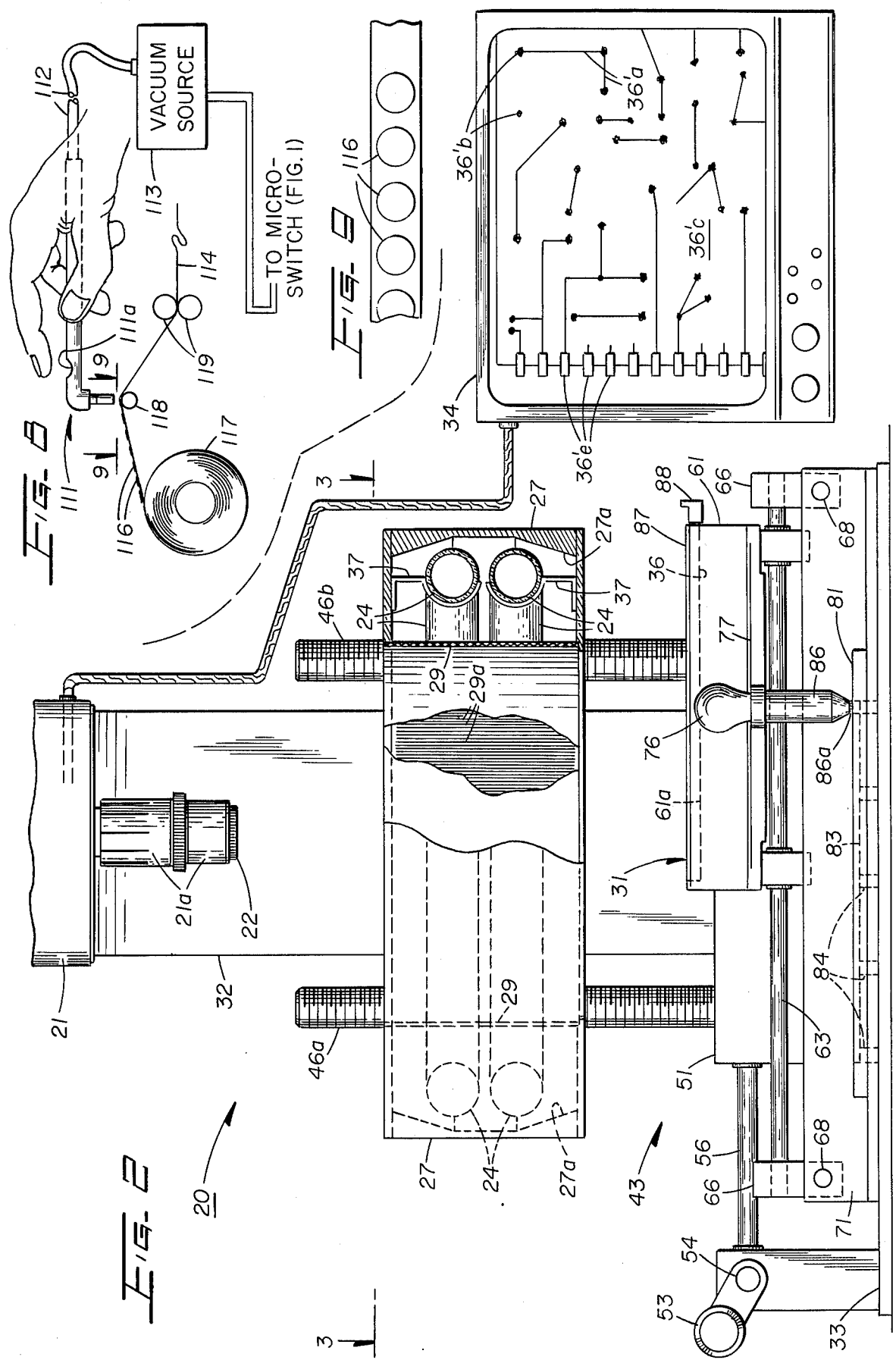
FIG. 2 is an enlarged, fragmentary front elevational detail view, partially in section, of the x-y table, light source polarized screen and camera employed in the video system of FIG. 1, together with a TV monitor coupled to the camera, with a partial pattern of typical circuit paths, terminals and soldered connections (bright spots) representative of a given printed circuit under examination being depicted on the monitor screen.
Figure 3:
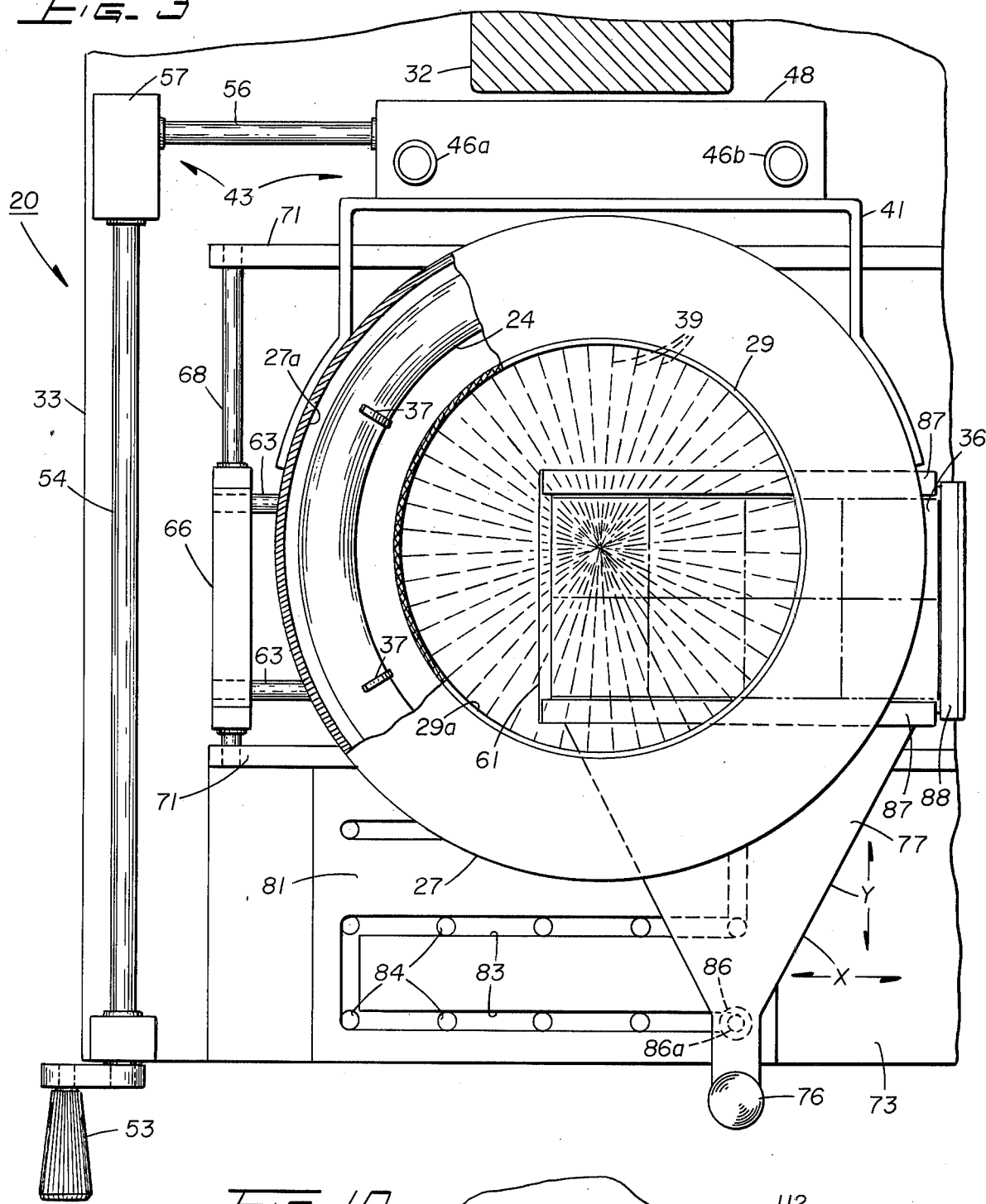
FIG. 3 is an enlarged, sectional detail view of the system of FIG. 1, excluding the camera, taken along the line 3—3 of FIG. 2, with the vertically polarized and radially directed light rays produced by the light source being shown pictorially by dashed lines and centered relative to a given x-y table-centered surface section of a printed circuit wiring board.

With particular reference first to FIGS. 1-3, there is depicted a composite video inspection system identified generally by the reference numeral 20. This system comprises a video camera 21, preferably having a polarized lens (or filter) 22 mounted adjacent the conventional camera lens system 21a, a light source 24, a reflector 27, a polarized screen 29, an X-Y table 31, and a video monitor 34 (see FIG. 2) coupled to the camera.

The camera 21 may be of conventional design, with one particular type found to be very effective for the purpose described herein being designated Model No. TC-1005/01, sold by RCA, Inc. This camera has 1000 line resolution, and is capable of providing excellent contrast between different types of light reflective surfaces, even in ambient light environments. The camera is mounted on a support stand 32 which is secured at its lower end to a main support plate 33. The monitor 34 may likewise be of conventional design, but one particular type having 1000 line resolution and found to be very effective for the intended purpose is designated Model No. EVM-1110R, sold by the Electrohome Company.

The polarized lens 22 is of a commercially available type and is rotatably mounted on the camera immediately adjacent the standard lens system 21a thereof. One preferred lens for the purpose intended is simply descriptively designated polarizing lens, sold by the Vivatar Company. This particular lens has been found to be capable of effectively highlighting selective light-reflective surface areas, such as solder fillets formed on a circuit board. Such high-lighting is optimized by adjusting the orientation of the polarized lens relative to the direction of the polarized light that is caused to impinge upon, and be reflected upward from the solder fillets toward the camera. The manner and significance of effectively discriminating not only between vertically and horizontally oriented reflected light, but between different degrees of vertically reflected light, will be discussed in greater detail hereinbelow.

The light source 24 in the illustrative embodiment of FIGS. 1-3 is comprised of two juxtaposed and substantially annular fluorescent lamps 24. These lamps are mounted adjacent the inner surface of the reflector 27, which has an enclosing cylindrical configuration. One particular type of lamp found to be very effective in the video system embodied herein is a 12 inch diameter Circle Line fluorescent lamp producing 32 watts of warm white light. It is understood, of course, that the diameter, wattage and type of light emitted by a given light source for a particular application will depend on a number of factors, such as the type of camera employed, the size and type of article to be examined in accordance with the principles of the present invention, and on the light conditions of the work environment. The lamps 24 are supported on the reflector 29 by means of a plurality of spaced spring clips 37 (only two seen in FIG. 2).

With respect to the reflector 27, it is of cylindrical configuration, with the inner surface thereof formed with a segmented concave inner surface 27a that results in the light produced by the lamps 24 being directed as substantially parallel light rays across the surface of the object to be examined, such as a circuit board 36 when properly positioned adjacent the lower peripheral edge of the polarized screen 29, as depicted in FIG. 4. The reflector 27 may be formed of any suitable light reflective material, such as aluminum, which is easily machined (to form the requisite inner surface), and polished to a relatively high gloss. With the lamps having 12 inch diameters in the illustrative embodiment, the reflector 27 was constructed to have an inside aperture-defining diameter of 8¼ inches, and an outside wall diameter of 13 inches.

As represented symbolically by the vertical lines 29a depicted in FIGS. 1 and 2, the polarized screen 29, which is suitably secured to a flanged base of the reflector 27, is preferably oriented so as to be vertically polarized. As such, the light that passes therethrough is formed into an infinite number of vertically oriented and radially directed planes. Each plane is, in turn, comprised of an infinite number of parallel light rays, all radially projected toward the center axis of the screen. Such rays are represented symbolically by the dashed lines 39 depicted in FIG. 3. It is understood, of course, that the vertical slots or windows in the screen are actually microscopic in terms of both width and spacing. One preferred screen material is sold by the Sargent/Welch Company, under the Registered trademark Poloroid Film.

As is best seen in FIGS. 1 and 3, the reflector 27 is mounted by a suitable bracket 41 to an adjustable gear driven light source support assembly designated generally by the reference numeral 43. This assembly is comprised of two upwardly extending threaded support rods 46a, b which threadably extend through two spaced and tapped bores formed in a support housing 48 which is secured to the bracket 41. The threaded rods 46 are rotatably journalled at their lower ends within a support member 51. Driving torque is applied to the threaded rods 46 through a suitable journalled crank arm 53, and coupled shafts 54 and 56. The latter shaft is coupled to the shaft 54 through a gear box 57 (FIG. 3) and to the threaded rods through conventional gearing in the lower support housing 48.

As thus described, and with reference again to FIG. 1, it is seen that the composite light source can be readily raised and lowered relative to the X-Y table-mounted circuit board 36 (or any other article), by simply rotating the crank handle 53 either clockwise or counterclockwise. It is obvious, of course, that the threaded rods could be motor driven, or if unthreaded, could serve as stationary guides, with the light assembly being raised and lowered by either cam-actuated mechanical or pneumatic means.

Considering the composite X-Y table 31 now in greater detail, it is comprised of an X-Y platform 61 that is dimensioned to accommodate a particular type of circuit board (or series thereof), and is preferably formed with a slightly recessed nesting area 61a (see FIG. 2). The platform is supported on a pair of guide rods 63 (see FIG. 3) that allow reciprocal displacement of the platform 61 in the X direction, as noted by arrows. The guide rods 63 are, in turn, supported at their common respective ends in different associated ones of a pair of support plates 66. Each plate has a bore extending longitudinally therethrough so as to accommodate a different one of a pair of guide rods 68 for relative movement therebetween. The guide rods 68 are, in turn, supported at their common respective ends in different associated ones of spaced support plates 71. The latter are both mounted on and secured to a subbase 73, with the latter mounted on the main support base 33 for the entire video system, with the exception of the monitor 34 in the illustrative embodiment.

As thus mounted on the spaced pair of guide rods 63 and 68, the X-Y platform 61 may be readily advanced along any desired X-Y coordinate grid pattern, for example. This is readily accomplished manually by providing a hand control knob 76 which is secured to a bracket 77 which, in turn, is secured to the X-Y platform 61, as best seen in FIGS. 1 and 3.

In accordance with an aspect of the invention, it is often desirous to examine only a discrete subsection of the printed circuit board 36 at any given time. This is particularly important when a substantially magnified (such as on the order of 5 times actual size) representation of a given circuit board section is desired to be examined. This may often be the case, for example, because of high density circuitry encompassed within a given sub-section of the board, or because of the possibility of even microscopic surface defects, such as scratches or pits, being of possible serious consequence.

In order to effect such sectionalized examination of the circuit board 36, a template 81 is secured to the subbase 73, and is formed with a predetermined number of spaced, parallel and laterally extending grooves 83, with each groove having a predetermined number of spaced detents or recesses 84 formed therein. A downwardly extending positioning member 86 (best seen in FIGS. 1 and 2), is secured at its upper end to the bracket 77, and is preferably formed with a spherical nose portion 86a at its lower end so as to facilitate the positioning thereof selectively within the various grooves 83, as well as into and out of the associated detents 84. Also to facilitate such placement of the positioning member 86, the bracket is preferably pivotally secured to the X-Y platform 61, with the weight of the bracket 77 and guide member 86, and/or separate biasing means (not shown) being employed to continuously exert a downward biasing force on the guide member 86.

It is appreciated, of course, that the bracket 77 could be rigidly secured to the platform 61, with the positioning member 86 mounted thereon in a spring-biased manner so as to allow the lower end thereof to be selectively positioned within any given detent 84, as well as associated groove 83. In such a case, it would be preferable to form the detents with gradually tapered walls, and the ends of the grooves 83 with tapered exit regions or ramps.

It should also be understood that any desired number of grooves 83 and detents 84 may be formed in the template 81 for any given application. In the illustrative embodiment, the template is formed to provide 15 indexable positions for the X-Y platform 61. For the particular circuit board illustrated, however, as seen in FIG. 3, only eight selected index positions will effectively subdivide the entire upper surface of the illustrative board relative to the pre-set range-of-view of the camera. It is appreciated, of course, that in order to subdivide any given circuit board into substantially equal sections, relative to a given camera, lens system and fixed pattern of grooves and detents formed in the template 81, it may be necessary not only to adjust the height of the camera relative to the board, but to provide adjustable peripheral guard rails on the X-Y platform 61. In this way each of a series of any given sized circuit board can be consistently placed at the proper position on the X-Y platform 61 for optimized sectionalized viewing by the camera 21. In the illustrative embodiment, a pair of side plates 87, secured to the raised side walls of the platform 61, define a confining channel in which the circuit board 36 may be readily inserted from the right side, as viewed in FIGS. 1–3. A suitable clamping member 88 is also shown as temporarily secured to one edge of the circuit board so as to facilitate the handling thereof. Member 88, however, is primarily employed to shield an array of gold plated terminals or pads therebeneath (not shown) while the board, in an earlier operation, is passed through a solder bath. A partial array of such terminals, designated 36'e, is shown along the opposite edge of a magnified, sectionalized portion of the circuit board displayed on the monitor 34 in FIG. 2.

In connection with the video system inspection of circuit boards, it may also be desirous in certain situations to utilize a standard reference pattern, formed on (or in) a suitable plate, mask or transparency, for the purpose of making readily identifiable test and reference pattern comparisons. Such a reference pattern may be formed in a number of different ways. For example, it may simply be formed as a plurality of spaced lines and dots (or circles), respectively representative of the circuit paths and soldered connections, on an opaque plate, and be positioned either to one side, or above or below, the screen of the TV monitor 34, or held by hand, in order to compare the reference and test patterns. Alternatively, the reference pattern could also be formed on a translucent or opaque plate, with suitably dimensioned slits and apertures formed therethrough in the areas corresponding to the circuit paths and soldered connections, respectively, on a given circuit board. Such a reference patterned plate, however, would not readily allow for the detection of possible random defects, such as solder bridges, icicles, or deleterious scratches or pits. Conversely, the reference pattern could also be readily coated on, embossed in, or otherwise formed on a transparency which advantageously would allow all areas of the board displayed on the monitor screen to be readily viewed.

In any of the above cases where the operator could view the monitor screen through the reference-patterned plate, mask or transparency, the latter in whatever form, identified generally by the numeral 93 in FIG. 14, may be optionally mounted on a pivotal holder 94, for example, secured to the outer housing of a monitor 34''. Such an arrangement allows the reference pattern to be easily and quickly positioned immediately adjacent the screen of the monitor, as well as interchanged as may be required for use in examining different codes of circuit boards, for example.

It should be appreciated, of course, that in many applications, even when rather complex circuitry with a relatively large number of soldered connections is involved, an experienced operator may quite readily and reliably memorize the locations of the soldered connections to be examined, as spatially represented by the aforementioned bright spots on the TV monitor. Concomitantly, an operator can also quite readily acquire the faculty to identify any abnormally positioned bright spots representative, for example, of an improperly clinched or oriented lead end, or a detrimental solder bridge that could possibly be shorting two adjacent printed circuit paths.

Considering now a typical circuit board inspection operation employing the video system 20, reference is first made to FIG. 4, where it is seen that the vertically polarized planes of light rays 39 that extend across the circuit board 36 not only impinge upon the substantially flat and vertically oriented sides or edges of the patterned printed circuit paths 36a, but also impinge upon the substantially higher, contoured surface areas of the one illustrated satisfactory soldered fillet 36b. Upon the polarized incident light rays 39 striking the latter, a substantial number of such rays are redirected upward as reflected light rays 39'. While the particular trajectories of the upwardly reflected light rays will depend on the particular angles of incidence thereof with the surface of a given solder fillet (or other raised or recessed area), it is seen that a substantial, concentrated number of such reflected light rays are directed to the camera 21, when positioned as depicted in FIGS. 1 and 2.

As previously briefly mentioned, it is such reflected light that is transformed into bright, sharply defined discrete white areas designated generally by the reference numeral 36'b on the screen of the TV monitor 34. These bright areas are advantageously vividly contrasted against the dark gray or black-lined paths 36'a that are representative of the normally non-vertically reflective, conductive circuit paths 36a. Any exposed areas of the eyelets (or pads) 36d on the circuit board would also appear as dark gray or black background areas on the monitor.

The profiled light reflective conductive surface areas 36b also appear on the monitor as areas 36'b in sharp contrast against the background 36'c representative of the nonconductive planar circuit board surface areas 36c. The latter background is typically considerably lighter than the displayed non-vertically reflective planar conductive surface areas, but distinctly darker than the discrete, bright areas 36b typically representative of the solder fillets. As viewed on the monitor screen, of course, the randomly spaced bright spots will correspond directly in spatial relationship with the number of solder fillets (bridges or icicles) confined within any given sectionalized area of the circuit board being examined.

With reference still to FIG. 4, a defective soldered connection is identified by the reference numeral 36b". This defective connection is shown, by way of example, in connection with a component 97 having a broken-off lead end 98. It is apparent that the small amount of solder associated with connection 36b" is of insufficient height, i.e., above the normal thickness of the circuit paths 36a, to cause any appreciable reflected light, if any, to be directed upwardly to the lens of the camera 21 (seen only in FIGS. 1 and 2). As a result, that particular defective area on the circuit board will be represented on the screen of the monitor as either an abnormally small and/or irregularly shaped bright spot, or more likely as a very dark gray or black area, in contrast to what should normally be a very bright spot. In either case, the defective soldered connection is readily identifiable.

As previously noted, bright spots on the monitor can also be established, of course, by raised light-reflective surfaces on the circuit board other than satisfactory soldered fillets. For example, if a component lead end, whether soldered or not, has not been properly cut to length, or clinched against the board, or improperly oriented, even when properly clinched, such defects will also appear on the TV monitor as identifiable bright areas. Each such bright area will correspond very closely with the actual configuration of the particular light-reflective surface condition that gave rise to such a displayed representation.

Similarly, any detrimental solder bridge, such as the one designated by the reference numeral 101 in FIGS. 5 and 6, that extends between two adjacent illustrative circuit paths 36a, can be readily detected on the monitor screen. This follows from the fact that such bridges typically project substantially above the adjacent circuit paths, and normally have an irregularly shaped, light reflective surface profile, as illustrated in FIG. 6. Such a profile gives rise to a substantial number of upwardly reflected light rays 39".

Figure 7:
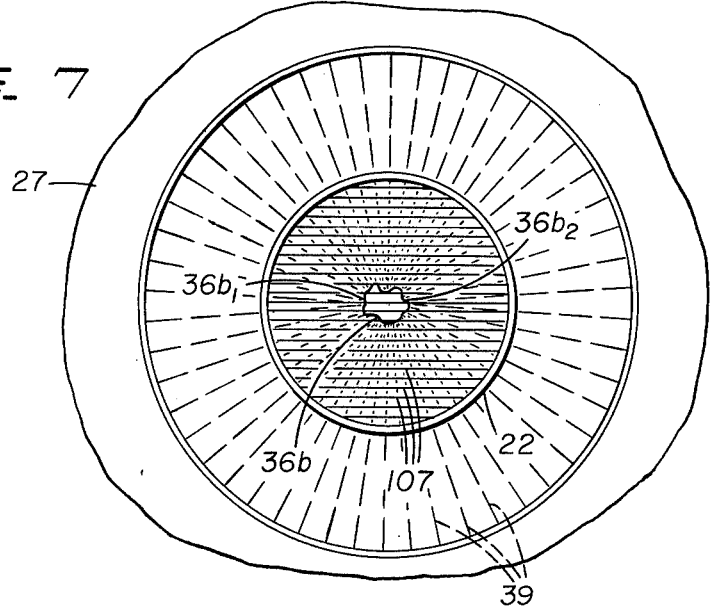
FIG. 7 is an enlarged, fragmentary plan view of a centered soldered connection on a circuit board as seen by the camera, through both the polarized lens attached thereto, and the light source, relative to the vertically polarized and radially extending light rays symbolically depicted by dashed lines, and produced in the video inspection system of FIGS. 1–3.

The significance of the polarized camera lens 22 on the camera will now be considered in greater detail. With particular reference to FIG. 7, it is recalled that the polarized light rays 39 from the annular fluorescent lamps 24 are directed radially inwardly, in vertically oriented planes, toward the circuit board area under examination. The polarized lens 22 as depicted, however, is oriented such that the symbolically shown array of parallel slits or windows 107 formed therein extend in only the X direction. As such, the camera 21 only clearly "sees" those surface portions or regions $36b_1$, $b_2$ of the illustrative solder fillet 36b that are diametrically disposed along an imaginary plane therethrough that is aligned with the particular orientation of the polarizing "windows" or "slits" 107 formed in the lens 22. It is understood, of course, that such windows are actually of microscopic dimensions.

As for the other raised and contoured surface regions circumferentially disposed about the solder fillet 36b in question, they will necessarily appear less bright than the highlighted areas for the particular orientation of the polarized lens illustrated. Normally, however, the diametrically opposed and highlighted areas of each properly camera-focused soldered fillet will be sufficient to ascertain, by the degree of brightness, and the size of the two-dimensional area displayed on the monitor screen, whether the soldered connection has been satisfactorily formed or not.

Nevertheless, in certain very demanding applications, it may be desirous to rotate the polarized lens 22 gradually through an angle up to 180°, while viewing the monitor, so that all circumferentially disposed surface regions of a given solder fillet under examination may be highlighted. This may be of particular importance when a given soldered connection, relative to a given polarizing lens setting, appears to be of marginal quality, as indicated selectively by the size, shape and brightness of the illuminated area representative thereof. Such polarized lens rotation may in certain instances also be beneficial in filtering out extraneous scattered reflected light from the "eye" of the camera. Gradual rotation of the polarized lens 22 can often also provide more significant information as to whether a given component lead end has been selectively properly clinched, oriented and cut to length.

The video system 20, of course, can also be used without a polarized lens 22. However, such a lens, for the reasons pointed out above, has been found to provide not only better contrast under a wider range of ambient light conditions, but better definition either of selected highlighted regions on, or of the entire surface profile of, the raised light reflective circuit board area(s) being examined.

In accordance with the principles of the present invention, it has also been found that the video system 20, when incorporating a rotatable polarized lens 22, is also very effective in locating microscopic imperfections in normally smooth, and even highly polished, light-reflective planar surfaces. More specifically, the video system 20 can effectively identify surface imperfections, such as detrimental scratches, pin holes or pits in otherwise smooth surfaces, such as the gold contact fingers or terminals typically formed along one or more edges of the circuit board 36. in the case of scratches, for example, they would appear as thin, bright, line segments on the TV monitor whenever the light source, reflector and polarized lens have selectively been properly oriented so as to optimize the amount of reflected light from such a defect received by the camera. Pin holes and pits would normally not require the same degree and/or frequency of rotation of the polarized lens 22 in order to identify such defects on the monitor screen.

Once a defective solder connection, or any other type of defect is ascertained as a result of the light-reflective characteristics thereof, it is generally desirous to suitably mark the circuit board 36 (or any other article) in some way for subsequent repair if possible. This may be most readily accomplished, of course, by simply using a suitable colored marking pencil or pen, and placing a mark or dot near each identified surface defect, preferably while viewing the magnified board section encompassing the defect on the monitor screen, so as to insure greater mark location accuracy.

The markings of colored pencils or pens, however, are quite unsightly if not removed, and in certain very sensitive electrical circuits, can actually affect the resistance and, hence, the operating characteristics thereof should such a marking extend between two very closely spaced active circuit paths or pads. The removal of such colored markings or dots generally has necessitated the use of small swabs soaked with water or some other suitable solvent, such as alcohol or perchlorethylene. This technique obviously is very time consuming, tedious and costly in operation.

Figure 10:
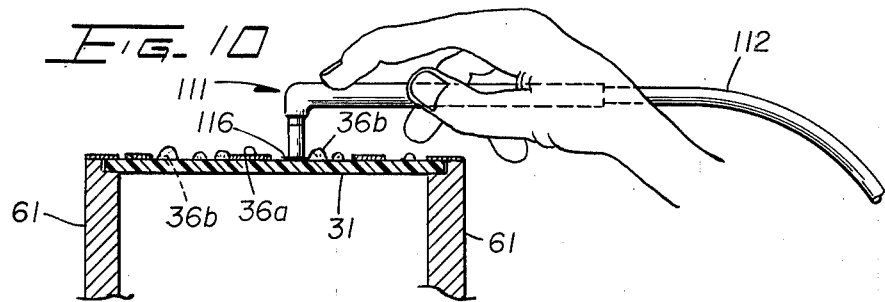
FIG. 10 is a pictorial view, partially in section, illustrating how an operator can readily secure an adhesive-backed, colored marking dot on a circuit board adjacent a defect with the vacuum-mechanism of FIG. 8.

In order to obviate the above problem of having to remove colored markings for one reason or another, the present invention, as disclosed in FIGS. 8–10, illustrates what is referred to herein as a vacuum tweezer-tape-dot technique for temporarily "marking" printed circuit board defects identified with one of the video systems embodied herein. Considered more specifically, and with reference first to FIG. 8, a finger-actuated vacuum tweezer designated generally by the reference numeral 111 is coupled through a line 112 to a vacuum source 113 shown only pictorially, and is positioned by hand over a carrier that may take the form of a thin plastic tape 114. The tape is employed to transport on at least one side thereof, exposed to the vacuum tweezer 111, an array of adhesive-backed pieces of colored plastic, preferably in the form of minute, circular colored dots 116 (see FIG. 9). Such plastic dots may be spaced in a longitudinally disposed row as illustrated, or may be formed in two or more rows, or spaced in some other patterned or random fashion on the tape carrier (or transport) 114. The latter may be payed off a supply reel 117, fed over and through suitably positioned guide rollers, such as the single roller 118 and mating rollers 119, respectively, and rewound on a take-up reel (not shown).

In order to facilitate the advancement of the tape carrier 114 at the rate at which the dots 116 are removed therefrom for marking, it is advantageous to have the tape carrier drive motor (not shown) controlled directly or indirectly by the operator. This may be readily accomplished by utilizing an actuable switch associated, for example, with a cradle (not shown) for supporting the vacuum tweezer when not in use, or by means of a suitable foot or hand-actuated electrical switch, with the switch in either case being connected within the electrical circuit for supplying power to the tape carrier drive motor. Alternatively, tape carrier advancement could also be readily controlled by a suitable vacuum-responsive transducer (not shown) coupled to the tweezer, and being responsively actuated upon sensing any change in the vacuum drawn therethrough. This would depend, of course, on whether a vacuum escape port 111a is open or closed by an operator's finger, as illustrated respectively in FIGS. 8 and 10.

With respect to the vacuum source 113, it may either be operated continuously, or automatically controlled by actuation of a switch associated with a cradle (neither shown) for supporting the vacuum tweezer 111 when not in use, or by a micro-switch 115 mounted on the camera support stand 32, for example, as depicted in FIG. 1. The latter switch, as illustrated, is actuated by engagement with a cam surface 115a whenever the reflector 27, supporting the polarized light source, is raised from the circuit board. To that end, power is preferably applied to the motor (not shown) in the vacuum source 113 only in response to the camera 21 and/or light source 24 being energized.

Regardless how the tape carrier 114 is indexably advanced, a given marking dot 116 can readily be removed from the tape carrier by an operator's finger being placed over the vacuum escape port 111a so that a relatively strong vacuum is established at the end of the vacuum tweezer (or nozzle) 111. Thereafter, the vacuum-held dot 116 may be readily carried by the hand-held tweezer 111 to the desired area on the circuit board, and placed immediately adjacent the previously identified defect, as pictorially depicted in FIG. 10. As previously mentioned in connection with marking pens or pencils, such dot placement would preferably be accomplished while viewing the TV monitor 34 so as to take advantage of the magnification made possible by the video systems embodied herein.

Upon placing a given adhesive-backed dot 116 on the circuit board, the operator's finger is thereafter removed from the escape port 111a so as to release the vacuum from the terminating end of the tweezer 111. By properly choosing the type of adhesive applied to the dots 116, they may be very easily and cleanly peeled off not only the tape carrier 114, but the circuit board after each defect identified thereby has been corrected. Moreover, by judiciously choosing any one of a number of commercially available adhesives that exhibit very low dielectric loss and resistance characteristics, the dots in many cases need not even be removed from the circuit board, even when they are in contact with one or more active circuit areas, unless desired for aesthetic reasons.

Figure 12:
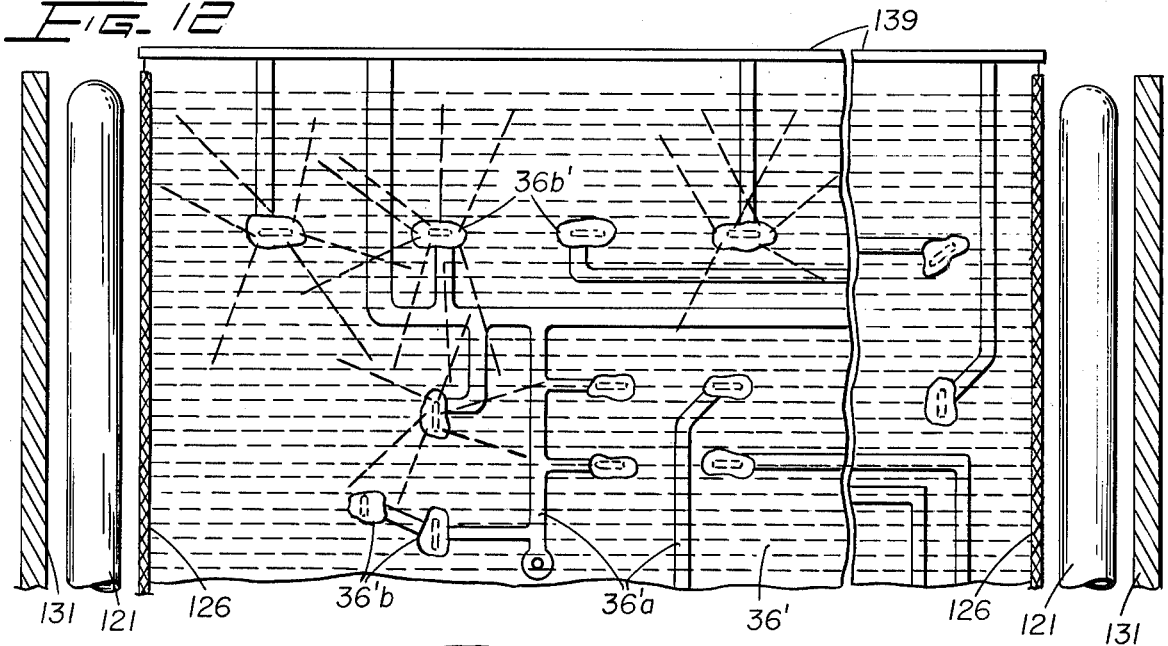
Figure 13:
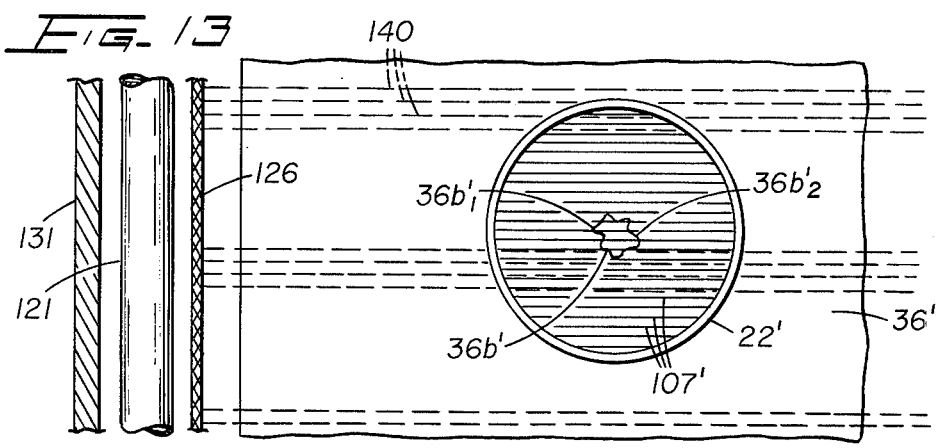
FIG. 13 is an enlarged, pictorial plan view of a centered soldered connection on a circuit board as seen by the camera, through the polarized lens attached thereto, relative to the vertically polarized and X-directed light rays symbolically depicted and produced by the video inspection system of FIG. 11.

FIGS. 11-13 illustrate several modifications that can be made to the video system 20 described in detail hereinabove. More specifically, in an alternative embodiment designated generally by the reference numeral 120, a pair of elongated, tubular incandescent lamps 121, as distinguished from the annular fluorescent lamps 24, are mutually disposed in parallel relationship so as to be adjacent opposite sides of an illustrative printed circuit board 36'. A pair of planar polarized screens 126, as distinguished from the cylindrical screen 29, are respectively positioned adjacent a different one of the lamps 121. A pair of outer parabolic reflectors 131 are respectively positioned adjacent a different one of the lamps 121 so as to direct the reflected and subsequently polarized light across the upper surface of the circuit board 36'. In all other structural respects the video system 120 is essentially identical to the video system 20 previously described, with the various other illustrated elements being identified by like, but primed, reference numerals.

Inasmuch as the polarized light from the elongated, tubular incandescent lamps 121 is directed as parallel extending rays 141 across the surface of the circuit board in only the X-direction, any raised projections on the circuit board, such as solder fillets 36b', are necessarily highlighted more vividly on the opposite sides thereof defined by an imaginary X-directed plane passing therethrough. Nevertheless, by gradually rotating the polarized lens 22' through an angle of 180° relative to a given light reflective solder fillet, for example, the entire silhouette of the latter can be vividly seen as a representative and distinctive spot 36'b' having various shades of brightness on the screen of the TV monitor 34'. Such a spot, of course, would be in contrast to the dark gray or black background displayed on the screen and representative of any exposed area of the associated eyelet or pad 36d', as well as other adjacent circuit path portions 36a' in the vicinity of each soldered connection under examination.

Gradual rotation of the polarized lens 22' may also be of importance in certain instances to filter out any detrimental, extranious scattered light rays, for example, from the eye of the camera. This may at times prove desirable even to highlight a portion of the surface profile of a given solder fillet more distinctly, i.e., with greater definition, than might otherwise be possible.

When elongated, tubular incandescent light sources are employed, it has been found that they are most effective if the light therefrom is directed onto the surface of the circuit board at a slight angle, such as about 10°, with tiltable light absorbing plates 139 (only one seen in FIG. 12) positioned on the sides of the circuit board not enclosed by the reflectors 131. Such light-absorbing plates, when dimensioned to have a height similar to that of the reflectors 131, and when formed with an inner surface having a textured or mat finish (preferably soft white in color), effectively facilitate the break-up or diffusion of any possible detrimental scattered light reflections that could otherwise impair the sharply defined representation of any particular three-dimensional area being viewed on the circuit board through the TV monitor 134' of FIG. 11.

The main advantages derived from utilizing the annular fluorescent bulbs 24, such as of the Circle Line type, as compared to the elongated incandescent light sources 121, are basically twofold. First, it has been found that unless special precautions are taken with respect to the infrared energy generated by the elongated incandescent lamps 121, even for low wattage ratings of the order of 40 watts, the adjacent polarized screens 127 may be damaged. Precautions necessary to prevent such damage may require an appreciable spacing between the light sources and the respective polarized screens, and/or forced air cooling (not shown), or a light transparent, heat isolating medium, such as a glass plate (not shown), interposed between each lamp 121 and the adjacent polarized screen.

Secondly, the utilization of annular type fluorescent lamps (preferably of the soft white type), when centered relative to, but spaced in elevation from the camera lens, provide a more uniform and effective distribution of light for more thorough examination on all sides of a given light-reflective projection on an otherwise planar surface of an article, with or without a rotatable polarized lens being used on the camera. Such a light source also produces a higher lumen level for a given wattage rating, as well as bulb size. As a result, the polarized lens 22 in the video inspection system 20 can normally be more effectively utilized as an adjustable camera "iris", i.e., to control the definition of a light-reflective surface area being examined on the monitor.

In summary, a method and several closed circuit TV video systems for use therewith have been disclosed which utilize, and rely on a unique relationship between, a specially oriented and polarized source of light, and a properly positioned polarized camera lens, to detect and discriminate between light reflective contoured projections and planar surfaces, or between planar surfaces and deleterious recessed areas, such as in the form of scratches, pin holes or pits on an otherwise normally smooth light reflective surface. Such a method and systems have been shown to have particular utility in inspecting printed circuit boards for various types of defects such as unsatisfactory soldered connections, improperly clinched, oriented or cut component lead ends, icicles, short-circuiting bridges, or circuit path discontinuities.

It is obvious that various modifications may be made in the particular method steps described herein, as well as in the structural arrangement of the illustrative video inspection system embodiments of the invention, and that a number of alternatives may be provided without departing from the spirit and scope of the present invention. For example, any short-circuiting solder bridges or icicles may be removed, and any defective solder connections may be touched-up or redone while the circuit board remains on the X-Y platform 61, and is being viewed in magnified form on the video monitor. The composite light source, polarized screen and reflector assembly would, of course, be raised to an elevated position above the circuit board for that purpose. In order to prevent any possible damage to the camera lens system and/or polarized screen(s) due to the heat generated from such a soldering operation, as well as any impairment in resolution of the displayed circuit pattern caused by molten solder-generated smoke, it is advisable to utilize a vacuum exhaust nozzle either mounted on and positioned very closely adjacent the tip end of the soldering iron, or otherwise positioned closely adjacent the circuit defect. Vacuum for this nozzle could advantageously be supplied by and under the control of the previously described vacuum source 113.

What is claimd is:

1. A video system for selectively ascertaining the presence and absence of, and for discriminating between, at least two distinctively different types of light-reflective surface areas formed on a common, exposed surface of a prepositioned object, one type of surface area being substantially two-dimensional, and the other type being substantially three-dimensional, said system comprising:

means for illuminating the exposed surface of said object with polarized light that extends across said surface such that in a direction at least substantially perpendicular thereto: (1) reflected light is minimized from those light-reflective areas on said surface having a substantially smooth, planar, two-dimensional profile, and (2) reflected light is maximized from those light-reflective areas on said surface having a three-dimensional profile;

video camera means positioned such that the axis of said lens thereof is oriented substantially perpendicularly to both the exposed surface of the object and the light ray paths of said polarized light for receiving the minimized and maximized patterns of reflected light from said respectively different types of surface areas, and for generating video signals that produce contrasting patterns representative thereof when displayed on the screen of a video monitor, and a video monitor electrically connected to said camera for producing said contrasting patterns.

2. A video system in accordance with claim 1 further comprising:

a polarized lens disposed between said camera and said object being viewed.

3. A video system in accordance with claim 2 wherein said means for producing polarized light rays comprises at least two mutually disposed light sources having axially disposed, elongated tubular bulbs confining elongated filaments therewithin, each bulb being positioned slightly above and extending in the direction of a different one of two opposed edges of said object, and polarized filter means positioned adjacent to and extending along the mutually opposed sides of said light sources, said filter means, in conjunction with said polarized lens when properly oriented, resulting in at least selected surface regions on any contoured three-dimensional surface areas being highlighted by said polarized light, and represented with maximum definition on the screen of said monitor.

4. A video system in accordance with claim 3 wherein said polarized filter means comprises a pair of substantially rectangular, planar polarized screens respectively positioned adjacent different ones of said light sources.

5. A video system in accordance with claim 2 wherein said means for producing polarized light rays comprises at least one light source with a substantially annular bulb dimensioned so as to circumscribe at least a predetermined surface portion of said object, and being positioned so as to overly the exposed surface to be examined, and polarized filter means of at least substantially cylindrical configuration positioned adjacent the inner circumference side of said light source, said filter means, in conjunction with said polarized lens when properly oriented, resulting in at least selected surface regions on any contoured three-dimensional surface areas being highlighted by said polarized light, and represented with maximum definition on the screen of said monitor.

6. A video system in accordance with claim 5 wherein at least said one light source comprises a fluorescent type lamp which is dimensioned to circumscribe the periphery of said object, and wherein said polarized lens is mounted on said camera and rotatably adjustable.

7. A video system in accordance with claim 4 wherein said light sources are of the incandescent filament type, and wherein said means for producing polarized light further includes a different reflector positioned adjacent the outer side of each of said light sources, and formed with an inner concave wall portion to direct concentrated reflected light across said exposed surface of said object at a desired angle relative thereto.

8. A video system in accordance with claim 5 wherein said means for producing polarized light further includes a cylindrical reflector positioned adjacent the outer side of said annular light source, and formed with a concave-defining inner wall portion to direct reflected light therefrom across the exposed surface of said object at a desired angle relative thereto.

9. A video system in accordance with claim 7 further comprising:

an indexable table mounted beneath said light source, and wherein said object comprises a printed circuit board mounted on said table so as to allow selective portions of said circuit board to be positioned within the focused and reflected-light-receiving range of said camera.

10. A video system in accordance with claim 8 further comprising:

an indexable table mounted beneath said light source, and wherein said object comprises a printed circuit board mounted on said table so as to allow selective portions of said circuit board to be positioned within the focused and reflected-light-receiving range of said camera.

11. A video system in accordance with claim 9 further comprising:

means to selectively displace said circuit board and the combination of said light source, polarized screens and reflector relative to each other so as to alter the spacing therebetween.

12. A video system in accordance with claim 10 further comprising:

means to selectively displace said circuit board and the combination of said light source, polarized filter means and reflector relative to each other so as to alter the spacing therebetween.

13. A video system in accordance with claim 11 wherein said surface areas on the printed circuit board having a substantially smooth, two-dimensional profile selectively comprise patterned circuit paths and terminals, which paths and terminals appear as dark gray areas on the screen of said monitor when operated in a black and white mode, whereas said surface areas having a contoured three-dimensional profile, such as satisfactory solder fillets, any abnormal solder bridges and icicles appearing randomly, and any scratches and pits in said normally smooth planar profiled surface areas, selectively and respectively appear as discrete, bright areas on said monitor screen.

14. A video system in accordance with claim 12 wherein said surface areas on the printed circuit board having a substantially smooth, two-dimensional profile selectively comprise patterned circuit paths and terminals, which paths and terminals appear as dark gray areas on the screen of said monitor when operated in a black and white mode, whereas said surface areas having a contoured, three-dimensional profile, such as satisfactory solder fillets, any abnormal solder bridges and icicles appearing randomly, and any scratches and pits in said normally smooth planar profiled surface areas, selectively and respectively appear as discrete, bright areas on said monitor screen.

15. A video system in accordance with claim 13 wherein a standard reference pattern, identifying the desired spatial locations of at least said circuit paths and desired solder connection areas associated therewith, is formed on a suitable medium which is mounted on said monitor, said reference pattern and medium being such as to allow direct, overlying comparison thereof with the circuit pattern being examined and displayed on said monitor screen.

16. A video system in accordance with claim 14 wherein a standard reference pattern, identifying the desired spatial locations of at least said circuit paths and desired solder connection areas associated therewith, is formed on a suitable medium which is mounted on said monitor, said reference pattern and medium being such as to allow direct, overlying comparison thereof with the circuit pattern being examined and displayed on said monitor screen.

17. A video system in accordance with claim 13 further comprising defect marking means, including indexable dot carrying transport means and vacuum controlled means, for successively picking up colored marking dots of suitable material from said transport means, and after transferring said vacuum-held dots respectively to each area on said circuit board identified as being defective by the particular reflected light pattern representative thereof displayed on said monitor, depositing each picked-up dot adjacent a different defective area by adjusting the magnitude of said vacuum applied against said dot.

18. A video system in accordance with claim 14 further comprising defect marking means, including indexable dot carrying transport means and vacuum controlled means, for successively picking up colored marking dots of suitable material from said transport means and transferring said dots respectively to each area on said circuit board identified as being defective by the particular reflected light pattern representative thereof displayed on said monitor, and depositing each picked-up dot adjacent a different defective area by adjusting the magnitude of said vacuum applied against said dot.

19. A video system for discriminating between two-dimensional and three-dimensional light-reflective patterned surface areas formed on an exposed, and at least substantially planar, surface of an article, said system comprising:

means for illuminating the exposed planar surface of said article with polarized light that extends across said surface such that in a direction at least substantially perpendicular thereto: (1) reflected light is minimized from those light-reflective areas on said patterned surface having a substantially smooth, two-dimensional profile, and (2) reflected light is maximized from those light-reflective areas on said surface having a three-dimensional profile;

video camera means positioned such that the axis of said lens thereof is oriented substantially perpendicularly to both the exposed planar surface of the article and the light ray paths of said polarized light, for receiving the minimized and maximized patterns of reflected light from said respectively different types of surface areas, and for generating video signals that produce contrasting patterns representative thereof when displayed on the screen of a video monitor; and a video monitor electrically connected to said camera for producing said contrasting patterns.

20. A video system in accordance with claim 19 wherein said means for producing polarized light comprises at least two mutually disposed light sources having axially disposed, elongated tubular bulbs confining elongated filaments therewithin, each bulb being positioned slightly above and extending in the direction of a different one of two opposed edges of said article, and polarized filter means positioned adjacent to and extending along the mutually opposed sides of said light sources, and wherein said video system further includes:

reflector means positioned adjacent the outer sides of said light sources, and formed with an inner concave wall portion dimensioned so as to direct concentrated reflected light across said exposed surface of said article at an angle relative thereto that results in at least selected regions on any contoured three-dimensional surface areas producing a substantial amount of reflected light toward said camera and, thereby, producing respective bright areas representative thereof on the screen of said monitor;

a rotatably adjustable polarized lens disposed between said camera and said article being viewed, and means to selectively displace said article and the combination of said light source, polarized filter means and reflector means relative to each other so as to alter the spacing therebetween.

21. A video system in accordance with claim 19 wherein said means for producing polarized light comprises at least one light source with a substantially annular bulb dimensioned so as to circumscribe at least a predetermined surface area of said article, and being positioned so as to overly the exposed surface to be examined, and polarized filter means of at least substantially cylindrical configuration positioned adjacent the inner circumference side of said light source, and wherein said video system further includes:

cylindrical reflector means positioned adjacent the outer side of said annular light source, and formed with a concave-defining inner wall portion to direct reflected light therefrom across the exposed surface of said object at a desired angle relative thereto that results in at least selected regions on any contoured three-dimensional surface areas producing a substantial amount of reflected light toward said camera and, thereby, producing respective bright areas representative thereof on the screen of said monitor;

a rotatably adjustable polarized lens disposed between said camera and said article being viewed; and means to selectively displace said article and the combination of said light source, polarized filter means and reflector means relative to each other so as to alter the spacing therebetween.

22. A video system in accordance with claim 20, further comprising:
an indexable table mounted beneath said light source, and wherein said article comprises a printed circuit board mounted on said table so as to allow selected portions of said circuit board to be positioned within the focused and reflected light-receiving range of said camera, and wherein said surface areas on the printed circuit board having a substantially smooth, planar two-dimensional profile selectively comprise patterned circuit paths and terminals, which paths and terminals appear as dark gray areas on the screen of said monitor when operated in a black and white mode, whereas said surface areas having a contoured three-dimensional profile, such as satisfactory soldered fillets, any abnormal solder bridges and icicles appearing randomly, and any scratches and pits in said normally smooth planar profiled surface areas, selectively and respectively appear as discrete, bright areas on said monitor screen.

23. A video system in accordance with claim 21 further comprising:
an indexable table mounted beneath said light source, and wherein said article comprises a printed circuit board mounted on said table so as to allow selected portions of said circuit board to be positioned within the focused and reflected light-receiving range of said camera, and wherein said surface areas on the printed circuit board having a substantially smooth, planar two-dimensional profile selectively comprise patterned circuit paths and terminals, which paths and terminals appear as dark gray areas on the screen of said monitor when operated in a black and white mode, whereas said surface areas having a contoured three-dimensional profile, such as satisfactory soldered fillets, any abnormal solder bridges and icicles appearing randomly, and any scratches and pits in said normally smooth planar profiled surface areas, selectively and respectively appear as discrete, bright areas on said monitor screen.

24. A method of discriminating between two-dimensional and three-dimensional light-reflective patterned surface areas formed on an exposed surface of an article, said method comprising the steps of:
illuminating the exposed surface of said article with polarized light that extends across said surface such that in a direction at least substantially perpendicular thereto: (1) reflected light is minimized from those light-reflective areas on said patterned surfaces having a substantially smooth, two-dimensional profile, and (2) reflected light is maximized from those light-reflective areas on said surface having a three-dimensional profile;
positioning a video camera above the exposed surface of the article, with the axis of the camera lens being oriented substantially perpendicularly to both the exposed surface and the light ray paths of said polarized light, for receiving the minimized and maximized patterns of reflected light from said respectively different types of surface areas, and for generating video signals, when energized, that are of the type to produce contrasting patterns representative of said respectively different types of surface areas on the screen of a video monitor, and
connecting a video monitor to the camera, energizing said monitor, and applying said video signals thereto so as to produce said contrasting patterns.

25. A method in accordance with claim 24 further comprising the steps of:
highlighting any region of a light-reflective surface area on the exposed article surface having a three-dimensional profile, and within the focused range of the camera, by interposing a polarized lens between said camera and the exposed surface of said article, and gradually rotating said polarized lens until the maximum amount of reflected light from any given three-dimensional surface area region is received by said camera, and converted in said camera and monitor into a vivid, brightly illuminated area on the screen of the latter.

26. A method in accordance with claim 25 further comprising the steps of:
selectively displacing the article surface to be examined along an X-Y coordinate plane relative to the camera so as to allow magnified, predetermined sectionalized areas thereof to be examined and, thereby, displayed with greater resolution on the screen of said monitor; and
selectively changing the spacing between the exposed article surface and the camera so as to selectively adjust the focus of said camera and to allow for a suitable marking to be made on the exposed surface of the article adjacent any two-dimensional or three-dimensional area thereof that appears on the monitor with an abnormal degree of brightness indicative of a defect.

27. A method in accordance with claim 26 further comprising the step of:
comparing a pre-formed standard composite reference pattern against the monitor-displayed contrasting patterns, representative of the camera-viewed composite pattern on the surface of said article, so as to readily ascertain all correspondingly similar patterned areas, as well as any dissimilar patterned areas.

28. A method in accordance with claim 26 further comprising the steps of:
picking up successively under vacuum control colored marking dots of suitable material from a dot-carrying support;
transferring said dots respectively to each area on said exposed article surface that is identified on said monitor as exhibiting particular light-reflective characteristics that make such an area of interest thereafter in the subsequent use of said article, and
depositing each picked-up dot adjacent a different one of said areas of particular interest by adjusting the magnitude of the vacuum applied against said dot.

29. A method of detecting a projection extending from a reference surface, wherein the projection has a reflecting surface that extends at least in part in a non-orthogonal direction toward said reference surface, which comprises the steps of:
projecting an annular array of polarized light rays toward said projection, with said polarized light rays being oriented in vertical and radially extending planes with respect to said reference surface, to reflect certain of said polarized light rays from said reflecting surface; and
generating a light image from at least a portion of the light rays of said polarized array thereof that are reflected, whereby said reflecting surface is readily discernable in said light image.

* * * * *